United States Patent [19]
Kellner

[11] Patent Number: 4,862,874
[45] Date of Patent: Sep. 5, 1989

[54] ENDOSCOPE FOR REMOVAL OF THROMBI FROM PULMONARY ARTERIAL VESSELS

[76] Inventor: Hans-Jörg Kellner, Panoramastrasse 2a, D-8902 Neusäss/West, Fed. Rep. of Germany

[21] Appl. No.: 204,359

[22] Filed: Jun. 9, 1988

[30] Foreign Application Priority Data

Jun. 10, 1987 [DE] Fed. Rep. of Germany ....... 3719250

[51] Int. Cl.$^4$ .............................. A61B 1/04; A61B 1/06
[52] U.S. Cl. ............................................ 128/6; 604/96
[58] Field of Search ................... 128/3, 4, 5, 6, 7, 328; 604/96, 97, 98, 99, 100, 101, 102, 103

[56] References Cited

U.S. PATENT DOCUMENTS 4,146,019  3/1979  Bass .......................................... 128/6
4,392,485  7/1983  Hiltebrandt ............................. 128/6
4,464,175  8/1984  Altman ................................. 128/4 X
4,619,247  10/1986  Inoue et al. ............................ 128/6

Primary Examiner—William H. Grieb
Attorney, Agent, or Firm—Pascal & Associates

[57] ABSTRACT

An endoscope having at least one light conductor, an image conductor and a rinsing channel, whereby the light and the image conductor as well as the rinsing channel open at a tip of an end part at the patient end of the endoscope, the end part of the endoscope tube being bilaterally turnable via Bowden wires, the end part being surrounded by a first dilatable ballon, a suction channel for connection to a suction pump having a diameter which is greater than the diameter of the rinsing channel extending in the endoscope tube, the suction channel also extending to the tip, and a catheter which extends beyond the tip extending in the endoscope tube, the catheter having a second dilatable balloon at its end.

6 Claims, 2 Drawing Sheets

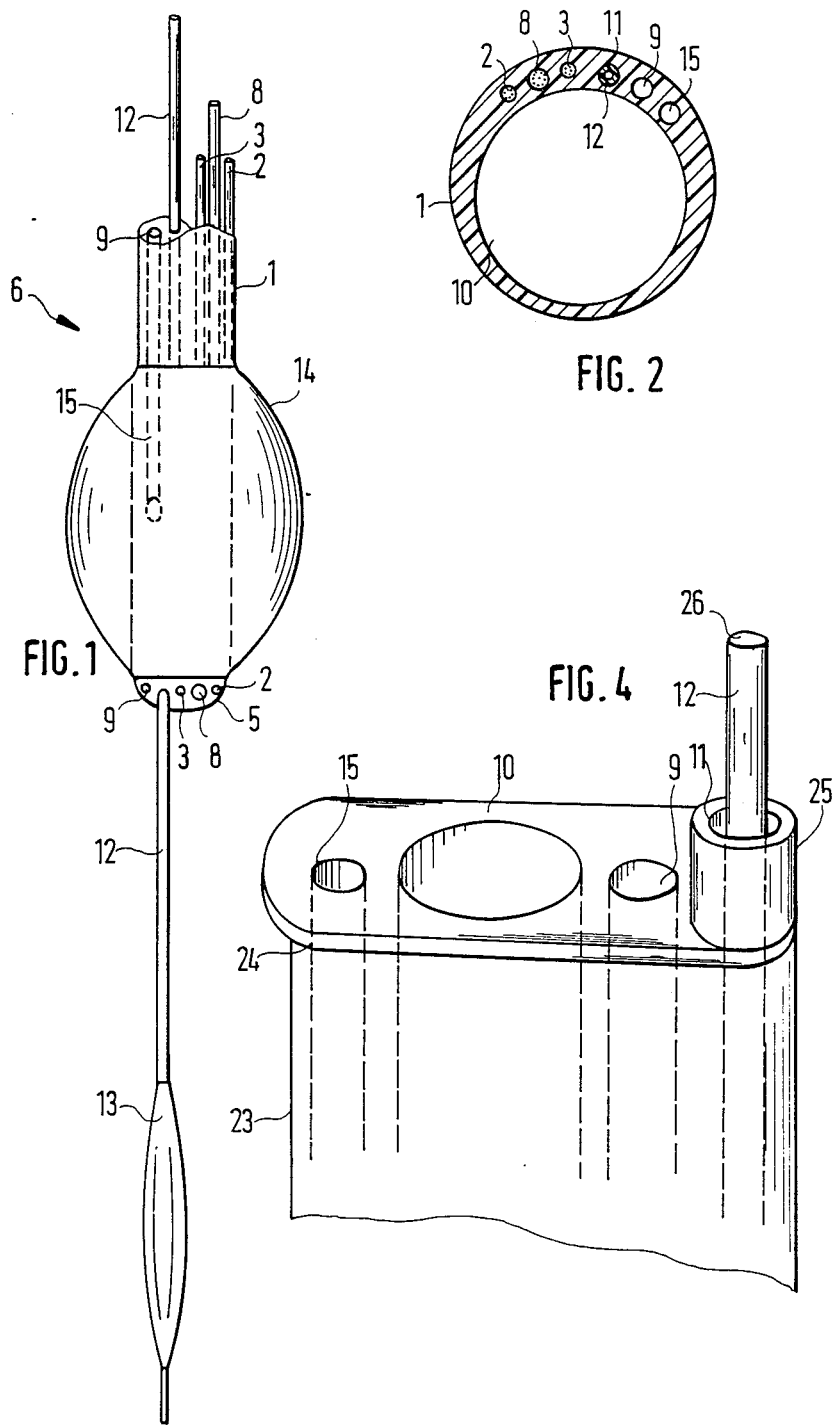

ENDOSCOPE FOR REMOVAL OF THROMBI FROM PULMONARY ARTERIAL VESSELS

The invention relates to an endoscope having at least one light conductor, an image conductor and a rinsing channel, whereby the light and the image conductor as well as the rinsing channel open at the tip of the end part of the pertinent end of the endoscope tube.

Endoscopes in the medical field are used primarily for diagnostics. In an endoscope at least one light conductor is attached to a cold light source and conducts light to the tip of the endoscope tube. A rinsing liquid is conveyed to the tip via a rinsing channel, the purpose of the rinsing liquid being to wash off body liquid, as for example blood, from the tip. An image received by the image conductor is conveyed to a lens system at the other end of the endoscope tube. It is known that, to carry out small dimension surgical operations, surgical tools can be attached to the head of the endoscope which can be controlled from the outside.

In surgical operations, in particular, in operations at the lower body extremities, the generation and removal of lung embolisms is a series problem. The source of embolizing thrombi are, most often, leg veins. These thrombi are impressed into the lung blood flow path via the heart and the pulmonary arteries; as a result, the lung blood flow paths become clogged. In light lung embolisms, a lysis therapy is used in which the clogged thrombi should dissolve. In difficult lung embolisms, an operation is necessary to surgically remove the thrombi, during which the patient must be connected to a heart-lung machine. In particular in difficult lung embolisms, the death rate is very high. The surgical removal of thrombi can only be undertaken in heart surgery centres. The first prerequisite in this instance is that the patient survive transportation to such a facility.

Aside from the high death risk, it should be noted that both methods of treatment are relatively expensive. A lysis treatment, which is usually carried out over a period of a week, is estimated to approximately U.S. $9,000.00. The estimated costs of an operation with use of a heart-lung machine amount to approximately U.S. $15,000.00 to U.S. $18,000.00.

An object of this invention is the design of the above-noted type of endoscope such that thrombi can be removed from the pulmonary arterial vessels with the endoscope.

In accordance with a preferred embodiment of this invention, an endoscope has at least one light conductor, an image conductor and a rinsing channel, whereby the light and the image conductor as well as the rinsing channel open at a tip of an end part of the patient end of the endoscope, the end part of the endoscope tube being bilaterally turnable via Bowden wires, the end part being surrounded by a first dilatable balloon; a suction channel having a diameter which is greater than the diameter of the rinsing channel extending in the endoscope tube; the suction channel which can be connected to a suction pump also opening at the tip, and a catheter which extends beyond the tip extending in the endoscope tube, the catheter having a second dilatable balloon at its end.

The endoscopic detection of thrombi and their removal by the same instrument can be carried out in almost every modern equipped hospital. With the first signs of a lung embolism, it is possible to immediately begin diagnosis and therapy for which only a small surgical incision is required in one of the neck veins. As a result, the often life threatening transportation of the patient to a heart surgery facility is no longer necessary. Moreover, the patient is not burdened with a large surgical operation as has, to this point, been the case of operations using a heart-lung machine. Since the instrument can be used repeatedly, the costs for removing a lung embolism are substantially lower than before, even in comparison with a lysis treatment.

An embodiment of the invention is described in greater detail below, with reference to the drawings, in which:

FIG. 1 is a side view of the front area of the endoscope;

FIG. 2 is a section through the endoscope tube;

FIG. 4 is a perspective view of a common coupling at which the channels open outside of the patient.

Figure 3:
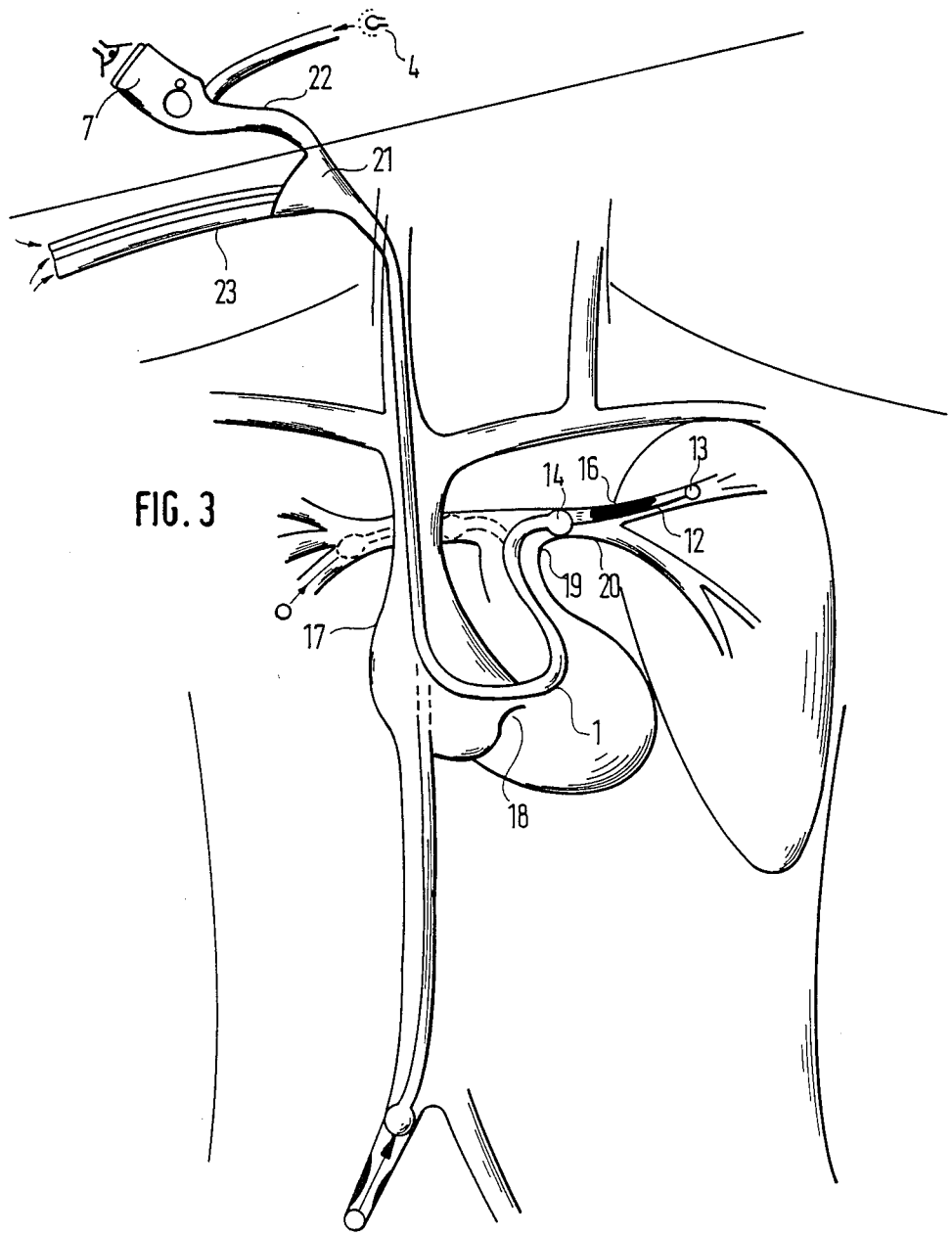
FIG. 3 is a schematic illustration of a patient to illustrate the procedure with a lung embolism and during removal of a thrombus in a leg vein.

The known endoscope tube 1 has two light conductors 2, 3 which are attached to a cold light source 4 outside of the patient. These light conductors 2, 3 open at the rounded tip 5 of the end part 6 at the patient end of the endoscope tube. An image conductor 8, which leads from the tip 5 to an optical examination system 7, extends between the two light conductors 2, 3. The known endoscope tube 1 has a rinsing channel 9 opening at the tip 5. It is possible to bilaterally turn the end part 6, which is about 10 cm long, by 120° via two Bowden wires which are not shown.

The above-noted features of the endoscope and its tube are known. The two light conductors 2, 3 each have a diameter of approximately 1.0 mm. The image conductor 8 is about 1.2 mm thick. The diameter of the rinsing channel 9 is about 1.0 mm.

A suction channel 10, whose diameter is between 6 mm and 8 mm, extends parallel to the conductors 2, 3, 8 and the rinsing channel 9. This suction channel also opens at the tip 2. In addition, a working channel 11, whose diameter is about 1.5 mm, extends parallel to the above-noted channels. A hollow catheter 12 extends through the working channel 11, which also opens at tip 2; the catheter 12 projects beyond tip 2 and has a dilatable balloon 13 at its end projecting beyond tip 2. The dilatable balloon 13 is shown in a collapsed state in FIG. 1.

The end part 6 at the patient end is surrounded by a dilatable balloon 14 which is shown in a liquid filled state in FIG. 1. A further channel 15, via which the balloon 14 can be filled or emptied, opens inside this balloon 14. This further channel has a diameter of approximately 1 mm.

As shown in FIG. 2, the suction channel 10 is disposed eccentrically to the outside diameter of the tube 1. The conductors 2, 3, 8 and the channels 9, 11, 15 are disposed in the thicker area of the wall of tube 1.

To remove an embolus 16 in a branch of the left pulmonary artery, an incision is made at the right neck vein and the endoscope tube is inserted there, if necessary, via a sluice. Balloon 14 and also balloon 13 of the already advanced Fogarthy catheter 12 are in a collapsed state. The tube is inserted into the right heart auricle, guided through the cardiac valve 18 and advanced through the right ventricle into the pulmonary artery 19. This takes place while being monitored by X-rays. If a contrast medium is now inserted into the pulmonary artery via rinsing channel 9, then the position of the embolus 16 can be detected via the X-ray monitoring. If this embolus 16 is lodged in a branch of the left pulmonary artery, then the end part 6 of the endoscope tube 1 is guided into the left pulmonary artery.

Balloon 14 is now dilated in the left pulmonary artery 20 by conveying liquid via channel 15. As a result, balloon 14 rests against the inner wall of artery 20. Rinsing liquid, which washes blood off the tip 2, is conveyed via rinsing channel 9. Under light observation, the Fogarthy catheter 12 is pushed through the obstruction with its balloon 13, which is still collapsed, and then also dilated by conveying liquid to balloon 13 via the inner part of catheter 12. Thrombus 16 can now be removed by suction via the suction channel 10. If this is a solid thrombus, then it is possible to convey a lysis liquid as softener via rinsing channel 9.

With thrombi which are stuck, it is possible to clear the vessel by means of balloon 13 of the Fogarthy catheter 12. In this case, catheter 12 with its dilated balloon 13 is pulled in direction of tip 2, after catheter 12 had first pierced the thrombus with collapsed balloon 13. In this way, the vessels can be cleared individually under light by means of catheter 12, as is, for example, also possible in leg veins, as indicated in FIG. 3.

The above-noted operations are carried out while monitoring the image delivered by the image conductor 8.

The endoscope tube 1 has a bifurcation outside of the patient. The light and image conductors 2, 3, 8, as well the bowden wires, which are not shown, for controlling the end part 6 at the patient end of the endoscope tube 1, extend in the one branch 22 of the bifurcation. In the other, sterile branch 23 of the bifurcation 21, the above-noted channels 9, 10, 11, 15 extend. These channels end at a common coupling 24. Channels 9, 10, 15 open at coupling 24 in one plane, while channel 11 ends at an extension piece 25 through which the Fogarthy catheter 12 is guided. This catheter 12 ends, for example, at a syringe through which balloon 13 can be filled or emptied via channel 26. A further coupling, which has channels corresponding to channels 9, 10, 15, can be slipped into coupling 24. The channel corresponding to channel 10 leads to a suction unit; rinsing or contrast liquid or a medication is conveyed via the channel corresponding to channel 10, while the liquid, with which balloon 14 is filled or emptied, is supplied or removed via the channel corresponding to channel 15.

The light conductor(s) 2, 3, as well as image conductor 8, can be disposed in a common channel of the endoscope tube 1. It is, moreover, possible to detach the one branch 22 together with the light and image conductors 2, 3, 8 from endoscope tube 1, which is discarded after use. The light and image conductors 2, 3, 8 are then inserted in a new, sterile tube 1 and branch 22 is mounted on this tube.

I claim:

1. An endoscope having at least one light conductor, one image conductor, a rinsing channel, a suction channel and a working channel, the light and the image conductor as well as the rinsing, the suction and the working channel being open at a tip of an end part at the patient end of the endoscope tube, the suction channel for connection to a suction pump having a diameter which is greater than the diameter of the rinsing channel, the end part of the endoscope tube being bilaterally turnable via Bowden wires, the end part being surrounded by a first dilatable balloon, a catheter being guided in a sliding manner in the working channel, said catheter extending beyond the tip and having a second dilatable balloon at its end, the endoscope tube having a bifurcation at its end opposite the end part at the patient end, the light and image conductor as well as the Bowden wires extending in one branch of the bifurcation, and the other branch of the bifurcation containing the remaining channels.

2. An endoscope according to claim 1, in which said other branch ends in a coupler which is common for the channel contained in said other branch.

3. An endoscope according to claim 2, in which the endoscope tube has a circular cross section, the suction channel being disposed eccentrically therein and the light and image conductor as well as the other channels extend in the thicker part of the tubing wall.

4. An endoscope according to claim 1, in which the light and image carrying conductors are guided in a common channel of the endoscope tube.

5. An endoscope according to claim 1, in which the one branch, together with the light and image conductors, are removable from the endoscope tube.

6. An endoscope according claim 1, in which the endoscope tube has a circular cross section, the suction channel being disposed eccentrically therein and the light and image conductor as well as the other channels extend in the thicker part of the tubing wall.

* * * * *